United States Patent

Bódi et al.

[11] Patent Number: 5,441,948
[45] Date of Patent: Aug. 15, 1995

[54] 1,3,4-BENZOTRAIZEPIN-5(4H)-ONE DERIVATIVES AND PROCESS FOR THE PREPARATION THEREOF

[75] Inventors: Ilona Bódi, Eger; Éva Gál, Budapest; Melinda Gál, Budapest; László Jaszlits, Budapest; Andrea Jednákovits, Szentendre; Adrina Kiss, Budapest; Anikó Miklós née Kovács, Budapest; György Máthé, Budapest; István Pallagi, Budapest; György Rabloczky, Budapest; Antal Simai, Budapest; Endre Tihanyi, Budapest, all of Hungary

[73] Assignee: Egis Gyogyszergyar Rt., Budapest, Hungary

[21] Appl. No.: 115,688

[22] Filed: Sep. 3, 1993

[30] Foreign Application Priority Data

Sep. 4, 1992 [HU] Hungary ................ 2833/92

[51] Int. Cl.⁶ ............... C07D 255/04; C07D 403/06; C07D 401/12
[52] U.S. Cl. ..................... 514/183; 540/501
[58] Field of Search .......... 540/501; 514/183

[56] References Cited

FOREIGN PATENT DOCUMENTS 57-109772 7/1982 Japan ................... 544/501

OTHER PUBLICATIONS

Omar, J. Het Chem 16, 1435 (1979).
Sunder, J. Het Chem 18, 1601–1604 (1981).
Tihanyi, Heterocycles 20, 571–574 (1983).
Barton, "Comprehensive Organic Chemistry" (Permagon Press) vol. 4, pp. 1024–1027 (1974).
Peet, J. Het Chem 21, 1807 (1984).
Davidson, Monat. Chem. 115, 565–571 (1984).
Davidson, Chem Abs 98, 179428u (1983).
Sakai, J. Pharm. Method. 5, 325–326 (1981).
Morgenstern, Pharmazie 47, 655 (1992).
Peet II, J Het. Chem. 21, 1817 (1984).

*Primary Examiner*—Mark L. Berch
*Attorney, Agent, or Firm*—Beveridge, DeGrandi, Weilacher & Young

[57] ABSTRACT

The invention relates to racemic or optically active 1,3,4-benzotriazepin-5(4H)-one derivatives, a process for the preparation thereof, pharmaceutical compositions comprising the same, to the use of the said compounds for the treatment of diseases and for the preparation of pharmaceutical compositions containing the said compounds as active agent.

The new compounds according to the invention correspond to the general formula (I),

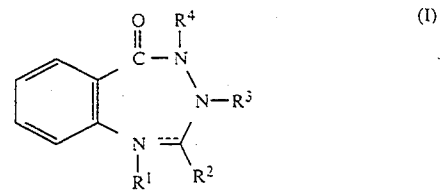

wherein
$R^1$ represents hydrogen or straight or branched chain $C_{1-4}$ alkyl optionally carrying a pyridyl or a phenyl substituent;
$R^2$ stands for cyanoimino;
$R^3$ denotes hydrogen or straight or branched chain $C_{1-4}$ alkyl;
$R^4$ stands for $C_{1-4}$ alkyl; and
the dotted line does not represent a valency bond; or
$R^2$ stands for a group of the formula $R^9R^{10}N$, wherein
$R^9$ and $R^{10}$ are independently hydrogen or straight or branched chain $C_{1-10}$ alkyl, or
$R^9R^{10}N$ together form a 5- to 7-membered heterocyclic group; or
$R^9R^{10}N$ together form a group of the formula $N=C(NR^{12}R^{13})NH_2$, wherein $R^{12}$ and $R^{13}$ are independently hydrogen or straight or branched chain $C_{1-10}$ alkyl, or
$NR^{12}R^{13}$ together form a 5- to 7-membered heterocyclic group;
$R^4$ stands for $C_{1-4}$ alkyl; and
the dotted line represents a valency bond, consequently substituent $R^1$ is missing;

(Abstract continued on next page.)

with the proviso that if $R^9$ and $R^{10}$ are the same, they are other than hydrogen.

The 1,3,4-benzotriazepin-5(4H)-one derivatives of the general formula (I) affect the circulatory system and possess antianginal, antihypertensive and peripheral vasodilating effects.

5 Claims, No Drawings

1,3,4-BENZOTRAIZEPIN-5(4H)-ONE DERIVATIVES AND PROCESS FOR THE PREPARATION THEREOF

This invention relates to racemic or optically active 1,3,4-benzotriazepin-5(4H)-one derivatives, a process for the preparation thereof, pharmaceutical compositions comprising the same, to the use of the said compounds for the treatment of diseases and for the preparation of pharmaceutical compositions containing the said compounds as active agent.

According to an aspect of the present invention there are provided racemic or optically active new 1,3,4-benzotriazepin-5(4H)-one derivatives of the general formula (I),

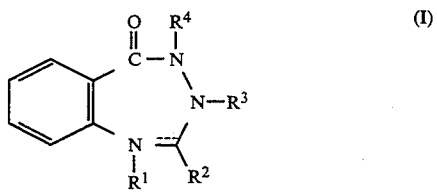

wherein $R^1$ represents hydrogen or straight or branched chain $C_{1-4}$ alkyl optionally carrying a pyridyl or a phenyl substituent, which latter may be substituted by a halogen atom or an alkoxy group;

$R^2$ stands for cyanoimino;

$R^3$ denotes hydrogen, straight or branched chain $C_{1-4}$ alkyl optionally substituted by a halogen atom or by a group of the formula $R^5O$ or $R^6R^7N$, wherein $R^5$ stands for hydrogen, pyridylcarbonyl or phenylcarbonyl optionally carrying a halogen or one or more alkoxy substituent(s), $R^6$ and $R^7$ are independently hydrogen or $C_{1-4}$ alkyl, or $R^6R^7N$ together form a 5- to 7-membered heterocyclic group optionally containing an oxygen atom or a group of the formula $R^8N$, wherein $R^8$ denotes hydrogen, $C_{1-4}$ alkyl or phenyl, which latter may optionally carry a halogen or an alkoxy substituent, or by a pyridyl or phenyl group optionally carrying a halogen or an alkoxy substituent;

$R^4$ stands for $C_{1-4}$ alkyl; and the dotted line does not represent a valency bond; or $R^2$ stands for a group of the formula $R^9R^{10}N$, wherein $R^9$ and $R^{10}$ are independently hydrogen; phenyl or straight or branched chain $C_{1-10}$ alkyl optionally substituted by a pyridyl or a phenyl group optionally carrying a halogen or an alkoxy substituent; or $R^9R^{10}N$ together form a 5- to 7-membered heterocyclic group optionally containing an oxygen atom or a group of the formula $R^{11}N$, wherein $R^{11}$ stands for hydrogen, $C_{1-4}$ alkyl or phenyl, which latter may optionally bear a halogen or an alkoxy substituent; or $R^9R^{10}N$ together form a group of the formula $N=C(NR^{12}R^{13})NH_2$, wherein $R^{12}$ and $R^{13}$ are independently hydrogen or straight or branched chain $C_{1-10}$ alkyl optionally substituted by a pyridyl group; or $NR^{12}R^{13}$ together form a 5- to 7-membered heterocyclic group optionally containing an oxygen atom or a group of the formula $R^{11}N$, wherein $R^{11}$ is as stated above;

$R^3$ stands for hydrogen, pyridylcarbonyl or $C_{1-4}$ alkyl, which latter may optionally be substituted by a group of the formula $R^{14}O$ or $R^{15}R^{16}N$, wherein $R^{14}$ represents pyridylcarbonyl or phenylcarbonyl optionally substituted by one or more alkoxy group(s), $R^{15}$ and $R^{16}$ independently denote hydrogen or $C_{1-4}$ alkyl, or $R^{15}R^{16}N$ together form a 5- to 7-membered heterocyclic group optionally containing an oxygen atom or a group of the formula $R^{17}N$, wherein $R^{17}$ represents hydrogen, $C_{1-4}$ alkyl or phenyl, which latter may optionally carry a halogen or an alkoxy substituent, or by a pyridyl or phenyl group optionally carrying a halogen or an alkoxy substituent;

$R^4$ stands for $C_{1-4}$ alkyl; and the dotted line represents a valency bond, consequently substituent $R^1$ is missing;

with the proviso that if $R^9$ and $R^{10}$ are the same, they are other than hydrogen, tautomers, racemic and optically active forms and possible mixtures thereof and the acid-addition salts of all these compounds.

The compounds according to the invention affect the circulatory system, more specifically they possess antianginal, antihypertensive and peripheral vasodilating effects.

To a preferred group of the compounds of the general formula (I) belong the compounds wherein the dotted line represents a valency bond; $R^2$ denotes alkylamino optionally carrying a pyridyl substituent, aminomethyleneamino optionally substituted by an alkylamino, piperidyl or homopiperazinyl substituent; $R^3$ stnds for hydrogen, $C_{1-4}$ alkyl carrying a pyridyl, trimethoxybenzoyl or phenylpiperazinyl substituent; and $R^4$ represents methyl.

Preferred representatives of the compounds of the general formula (I) are the following derivatives:

2-[amino-(1-piperidinyl)-methyleneamino]-4-methyl-3,4-dihydro-1,3,4-benzotriazepin-5(4H)-one, 2-[amino-(3,3-dimethyl-2-butylamino)-methyleneamino]-4-methyl-3,4-dihydro-1,3,4-benzotriazepin-5(4H)-one, 2-[amino-(1-homopiperazinyl)-methyleneamino]-3-[3-(3,4,5-trimethoxybenzoyloxy)-1-propyl]-4-methyl-3,4-dihydro-1,3,4-benzotriazepin-5(4H)-one, 2-(3,3-dimethyl-2-butylamino)-4-methyl-3,4-dihydro-1,3,4-benzotriazepin-5(4H)-one, 2-[amino-(1-piperidinyl)-methyleneamino]-3-(2-pyridylmethyl)-4-methyl-3,4-dihydro-1,3,4-benzotriazepin-5(4H)-one, 2-(3-pyridylmethylamino)-3-[3-(4-phenyl-1-piperazinyl)-1-propyl]-4-methyl-3,4-dihydro-1,3,4-benzotriazepin-5 (4H)-one, and pharmaceutically acceptable acid-addition salts thereof.

2-Cyanoimino-, 2-(substituted amino)- and 2 -aminomethyleneamino-1,3,4-benzotriazepin-5 (4H)-one derivatives have not so far been described in the technical literature and the known 2-amino-1,3,4-benzotriazepin-5(4H)-ones belong to a group of compounds which has so far been less studied.

The synthesis of 2-amino-3,4-dihydro-4H-1,3,4-benzotriazepin-5-one is described in J. Pharm. Sci. [R. W. Leiby et al.: J. Pharm. Sci. 65(4), 605 (1977)] and in the published Japan patent application No. 82-109,772 (C.A. 97, 216,249p). According to these references 2-aminobenzhydrazide derivatives are cyclized with bromocyane and with carbon disulfide, respectively. The further substitution reactions of the thus-obtained 2-amino compounds are not described, the structure of the single described monosubstituted 2-amino derivative, namely the 2-phenylamino-3,4-dihydro-4H-1,3,4-benzotriazepin-5-one [A. M. E. Omar et al.: J. Het. Chem. 16, 1435 (1979)], has proved to be erroneous [S. Sunder et al.: J. Het. Chem. 18, 1601 (1981)]. This compound has not been prepared so far.

It is known that in many countries of the world more and more people suffer from cardiovascular diseases peculiar to civilized communities. Among these diseases angina pectoris, hypertension and asthma afflict a considerable part of the population. For the treatment of these illnesses smooth muscle relaxants having a selective effect on the heart and lungs would be necessary. Compounds possessing $K^+$-channel-opening effect could meet these requirements [A. H. Weston: Drug News Perspectives 1, 205 (1988)]. According to pharmacological and clinical trials these substances possess bronchus- and coronary-dilating effects and in the treatment of angina pectoris their activity has proved to be more durable than that of the nitrate compounds.

Surprisingly it has now been found that the new 1,3,4-benzotriazepines according to the invention considerably reduce the time necessary to a 50% and 90% repolarization of the heart's action potential, that is they exert $Ca^{2+}$ antagonist and $K^+$-channel-opening effects. This double character of activity may be very advantageous in the therapy, as the $Ca^{2+}$-antagonist component may alleviate the unpleasant side-effects (tachycardia and the so-called "first dose effect") characteristic of drugs having merely $K^+$-channel-activating activity (e.g. Pinacidil).

According to a further aspect of the present invention there is provided a process for the preparation of racemic or optically active new 1,3,4-benzotriazepin-5(4H)-one derivatives of the general formula (I), wherein $R^1$, $R^2$, $R^3$, $R^4$ and the dotted line are as stated above, which comprises a) for the preparation of compounds of the general formula (I), wherein the dotted line does not represent a valency bond, $R^2$ stands for cyanoimino and $R^1$, $R^3$ and $R^4$ are as stated above for the compounds of the general formula (I) containing a single valency bond between the N(1) and C(2) atoms, reacting a compound of the general formula (II),

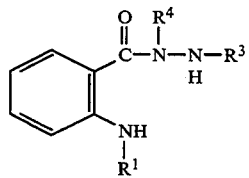

wherein $R^1$ $R^3$ and $R^4$ are as stated above, with a compound of the general formula (III),

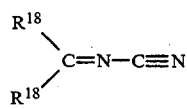

wherein $R^{18}$ stands for alkylthio ar aryloxy; or b) for the preparation of compounds of the general formula (I), wherein the dotted line does not represent a valency bond, $R^2$ denotes cyanoimino and $R^1$, $R^3$ and $R^4$ are as stated above for the compounds of the general formula (I) containing a single valency bond between the N(1) and C(2) atoms, with the proviso that $R^1$ and/or $R^3$ is/are other than hydrogen, reacting a compound of the general formula (I), wherein the dotted line does not represent a valency bond, $R^2$ stands for cyanoimino, $R^1$ and/or $R^3$ represent(s) hydrogen and $R^4$ is as stated above, with a compound of the general formula (IV),

wherein $R^{19}$ has the same meaning as $R^1$ and/or $R^3$ given above for the compounds of the general formula (I) containing a single valency bond between the N(1) and C(2) atoms except that it may not stand for hydrogen, X denotes halogen, methanesulfonyloxy, p-toluenesulfonyloxy or any other leaving group; or c) for the preparation of compounds of the general formula (I), wherein the dotted line represents a valency bond, consequently $R^1$ is missing, and $R^2$, $R^3$ and $R^4$ are as stated above for the compounds of the general formula (I) containing a double bond between the N(1) and C(2) atoms, reacting a compound of the general formula (I), wherein the dotted line does not represent a valency bond, $R^2$ stands for cyanoimino and $R^1$, $R^3$ and $R^4$ are as stated above for the compounds of the general formula (I) containing a single valency bond between the N(1) and C(2) atoms,,with an amine of the general formula (V),

wherein $R^9$ and $R^{10}$ are as stated above; or d) for the preparation of compounds of the general formula (I), wherein the dotted line represents a valency bond, consequently $R^1$ is missing, $R^3$ stands for pyridylcarbonyl and $R^2$ and $R^4$ are as stated above for the compounds of the general formula (I)-containing a double bond between the N(1) and C(2) atoms, acylating a compound of the general formula (I), wherein the dotted line represents a valency bond, $R^3$ is hydrogen and $R^2$ and $R^4$ are as stated above, with a carboxylic acid of the general formula (VI),

wherein $R^{20}$ stands for pyridyl, or with a reactive derivative thereof; or e) for the preparation of compounds of the general formula (I), wherein the dotted line represents a valency bond, consequently $R^1$ is missing, $R^3$ is hydrogen and $R^2$ and $R^4$ are as stated above for the compounds of the general formula (I) containing a double bond between the N(1) and C(2) atoms, with the proviso that $R^2$ is other than a group of the formula $N=C(NR^{12}R^{13})NH_2$, subjecting a compound of the general formula (II) to cyclization, wherein $R^1$ stands for hydrogen and $R^3$ denotes a group of the formula $-C(=S)-NR^9R^{10}$, wherein $R^9R^{10}N$ is as stated above, with the proviso that it may not stand for a group of the formula $N=C(NR^{12}R^{13})NH_2$;
and, if desired, converting a basic compound of the general formula (I), wherein $R^1$, $R^2$, $R^3$, $R^4$ and the dotted line are as stated above, obtained according to process variants a)-f) into an acid-addition salt thereof.

According to a preferred embodiment of process variant a) a carboxylic acid hydrazide derivative of the general formula (II) is reacted with a cyanoiminodithiocarboxylic acid ester of the general formula (III), wherein $R^{18}$ stands for alkylthio, in an excess of 10 to 100 molar % of the ester, at a temperature between 50° C. and 140° C., preferably at the boiling point of the reaction mixture. A polar solvent, preferably an alcohol, is used as solvent. The reaction can be accelerated by adding a tertiary amine to the mixture.

According to a preferred embodiment of process variant b) compounds of the general formula (I) alkylated in the place of $R^1$ and/or $R^3$ are prepared by reacting a compound of the general formula (I) containing hydrogen as $R^1$ and/or $R^3$ with an alkylating agent, preferably with an alkyl halide or with any other alkyl compound containing a leaving group (e.g. with a tosylate or mesylate), in a polar aprotic solvent, preferably in dimethylformamide, in the presence of a base, at a temperature between 20° C. and 100° C.

According to a preferred embodiment of process variant c) compounds of the general formula (I), wherein $R^2$ denotes an unsubstituted amino, are prepared by reacting a compound of the general formula (I) containing a cyanoimino substituent as $R^2$ with an amine of the general formula (V) applied in an excess of 10 to 100 molar % in a polar solvent, at a temperature between 50° C. and 140° C., preferably at the boiling point of the solution.

According to a preferred embodiment of process variant d) compounds of the general formula (I) containing pyridylcarbonyl as $R^3$ are prepared by reacting a compound of the general formula (I), wherein $R^3$ represents hydrogen, with a reactive derivative (preferably chloride) of a carboxylic acid of the general formula (VI) in an inert organic solvent, optionally in the presence of a tertiary amine, at a temperature between 0° C. and 70° C.

According to a preferred embodiment of process variant e) compounds of the general formula (I), wherein $R^2$ stands for substituted amino, are prepared by subjecting a compound of the general formula (II) containing a group of the formula $-C(=S)-NR^9R^{10}$ as $R^3$ to cyclization in an inert organic solvent, preferably with the aid of dicyclohexylcarbodiimide, at a temperature between 50° C. and 140° C., preferably at the boiling point of the reaction mixture.

The reaction mixture obtained according to any of the above process variants can be worked up by methods known per se, e.g. the excess of the reagent and/or solvent is removed (optionally in vacuo) and the residue is extracted and/or subjected to chromatography and/or crystallization.

Some compounds of the general formula (II) used as starting substances for process variant a) are known in the art [R. W. Leiby: Synth. Commun. 6(4), 295 (1976)]. Those compounds of the general formula (II) which have not so far been described in the literature can be prepared by analogous methods.

The reagents of the general formulae (III), (IV), (V) and (VI) used for the reaction according to the invention are known in the art [e.g. R. J. Timmons et al.: J. Org. Chem. 32, 1566 (1967); K. Schlögl et al.: Monatshefte für Chem. 95, 922 (1964); Beilsteins Handbuch der organischen Chemie 4, 193, III. 367, IV. 730, Springer Verlag; Houben-Weyl: Methoden der organischen Chemie, E5/1, 587, G. Thieme Verlag Stuttgart—New York (1985)].

The valuable pharmaceutical properties of the new compounds according to the invention are shown by the following experiments.

I. Intracellular electrophysiological studies on isolated canine Purkinje fibres: study of the characteristics and the duration of the action potential Mongrel dogs of both sexes, weighing 8–22 kg, were anaesthetized with intravenously administered sodium pentobarbital, 30 mg/kg (Nembutal ®). The superficial Purkinje fibres were excised from the heart and placed in plastic organ bath containing Tyrode's solution (147.0 nM of $Na^+$, 4.0 mM of $K^+$, 133.3 mM of $Cl^-$, 2.0 mM of $Ca^{2+}$, 22.0 mM of $HCO_3^-$, 0.9 mM of $H_2PO_4^+$, 0.7 mM of $Mg^{2+}$, 5.0 mM of glucose) The perfusate (Tyrode's solution) was gassed with a mixture of 95% of $O^2$ and 5% of $CO_2$. Temperature of the organ bath was 37.0°±0.5° C. pH=7.3±0.5. Purkinje fibres were incubated for 1–2 hours in order to avoid spontaneous changes in the duration of action potential, to be observed often for a short period after the preparation completed. Conventional glass microelectrode method was used to measure intracellular action potentials. The electrodes were filled with 3M KCl solution, resistance was 5–15 Mohm. Microelectrodes were connected to high input-resistance capacity-neutralizing amplifier through a Ag-AgCl connection. Another electrode was placed in the organ bath as a reference electrode. Maximum rate of depolarization ($V_{max}$) was measured with an electronic differentiating unit. The intracellular pulses were visualized on a two-channel oscilloscope by a microcomputer in on-line mode. The following parameters were measured: resting potential, action potential amplitude, 50% and 90% repolarizations, maximum rate of depolarization. Preparations were stimulated through silver electrodes insulated with PTFE. Parameters of stimuli were rectangular pulses of 1 ms duration with an intensity of two times the threshold. The basal stimulation periods were changed between 200 and 1000 msec. [Varré et al., J. Cardiovasc. Pharmacol. 11, 251 (1988)]. The results are shown in the following Table I.

TABLE I

| | Effect of compounds of general formula (I) on the action potential | | | | | |
|---|---|---|---|---|---|---|
| Compound | $ARD_{50}$ (msec) | | | $ADD_{90}$ (msec) | | |
| (No. of Example) | before treatment | after treatment | Change (%) | before treatment | after treatment | Change (%) |
| 4 | 169 | 113 | −33 | 250 | 226 | −10 |
| 17 | 158 | 91 | −42 | 253 | 221 | −13 |
| 18 | 156 | 111 | −29 | 251 | 213 | −15 |
| 19 | 161 | 121 | −25 | 259 | 237 | −9 |

TABLE I-continued

| | Effect of compounds of general formula (I) on the action potential | | | | | |
|---|---|---|---|---|---|---|
| Compound | ARD$_{50}$ (msec) | | | ADD$_{90}$ (msec) | | |
| (No. of Example) | before treatment | after treatment | Change (%) | before treatment | after treatment | Change (%) |
| 20 | 137 | 79 | −42 | 238 | 227 | −5 |
| 22 | 159 | 97 | −39 | 242 | 219 | −10 |
| Pinacidil | 181 | 71 | −61 | 258 | 141 | −45 |
| Nicorandil | 180 | 107 | −41 | 265 | 179 | −32 |

The applied dose of the compounds according to the invention is 10 mg/L.
Concentration of Pinacidil: 1 mg/L
Concentration of Nicorandil: 5 mg/L
APD: action potential duration II. Inhibitory effect on the vasopressin-induced ST elevation in anaesthetized rats The studies were performed in 200–250 g CFY male rats. Animals were anaesthetized with intraperitoneally administered urethane (1 mg/kg), then subjected to ECG, using limb leads. Coronary spasm, reflected by elevated ST deflection in the ECG recordings, was induced by treating the rats with 3 IE/kg of vasopressin intravenously. It was examined whether the intravenous pretreatment of animals with the compounds according to the invention inhibited the vasopressin-induced ST elevation; inhibition indicated ceased hypoxia, i. e. an antianginal effect [J. Pharm. Methods. 5, 325–336 (1981)].

TABLE II

| Inhibitory effect of compounds according to the invention on the vasopressin-induced ST elevation | |
|---|---|
| Compound (No. of Example) | Inhibition (%) |
| 4* | −36 |
| 17 | −68 |
| 19 | −59 |
| 22 | −59 |
| Nicorandil | −12 |
| Niocorandil* | −60 |

Dose of compounds of the invention: 1 mg/kg, i.v. except where appears
*: 5.0 mg/kg i.v.

The data in Tables I and II indicate that the compounds according to the invention considerably reduced the time interval necessary to the cardiac repolarization and significantly inhibited the vasopressin-induced ST elevation. Accordingly, the compounds of the general formula (I) can be used to treat cardiovascular disorders, especially angina pectoris and hypertension. The K$^+$-channel-opening (APD$_{90}$ decreasing) property of these compounds is an additional benefit to their therapeutic value.

Toxicity of the compounds is usually low. These features as a whole are indicators of valuable therapeutic spectrum and safety. For therapeutic reasons, daily doses of the compounds according to the invention usually range from 0.2 to 25, preferably from 0.2 to 10, mg/kg bodyweight. In particular cases, daily quantities are administered in split doses, with regard to the absorption conditions.

According to a further aspect of the present invention there are provided pharmaceutical compositions comprising as active ingredient a pharmaceutically effective amount of a racemic or optically active compound of the general formula (I), the tautomers and/or acid-addition salts thereof together with one or more pharmaceutically acceptable carrier(s), diluents and/or excipient(s).

The pharmaceutical compositions of the present invention can be prepared by methods known per se by admixing the active ingredient with suitable inert solid or liquid carriers, diluents and/or excipients and bringing the mixture to galenic form.

The pharmaceutical compositions of the present invention may be suitable for oral (e. g. tablet, pill, coated pill, dragée, solid or soft gelatin capsule, solution, emulsion or suspension), parenteral (e.g. injection solution) or rectal (e.g. suppository) administration.

For the preparation of tablets, coated tablets, dragées and solid gelatin capsules e.g. lactose, corn starch, potatoe starch, talc, magnesium carbonate, magnesium stearate, calcium carbonate, stearic acid or the salts thereof, etc. can be used as carrier. As carriers for the soft gelatin capsules e. g. vegetable oils, fats, waxes or polyols of suitable consistency can be used. For the solutions and syrups e.g. water, polyols (polyethylene glycol), saccharose or glucose can be used as carrier. The injection solutions can comprise e.g. water, alcohols, polyols, glycerol or vegetable oils as carrier. The suppositories can be prepared with the aid of e. g. oils, waxes, fats or polyols of suitable consistency.

In addition, the pharmaceutical formulations may comprise auxiliaries Usually applied in the pharmaceutical industry, e.g. wetting, sweetening agents, aroma substances, salts causing the change of osmotic pressure, buffers etc.

According to a further aspect of the present invention there is provided the use of the compounds of the general formula (I), tautomers and/or acid-addition salts thereof for the preparation of pharmaceutical compositions having particularly antianginal, antihypertensive and peripheral vasodilating effects.

According to a still further aspect of the present invention there is provided a method of cardiovascular treatment, which comprises administering to the patient an effective amount of a compound of the general formula (I), a tautomer or a pharmaceutically acceptable salt thereof.

The invention is further illustrated by the following Examples of non-limiting character.

EXAMPLE 1

2-Cyanoimino-4-methyl-1,2,3,4-tetrahydro-4H-1,3,4-benzotriazepin-5-one (Method A)

A solution of 16.5 g (0.1 mole) of 2-amino-N-methyl-benzoic acid hydrazide and 16.1 g (0.11 mole) of dimethyl N-cyanodithioiminocarbonate in 165 ml of propanol is boiled under stirring and reflux cooling for 24 hours. Then it is cooled and allowed to crystallize at 0° C. for 24 hours. The crystals are filtered off to obtain 16.5 g of the desired product. When evaporating the filtrate, further 1.2 g of product are obtained.

Yield: 83%, m.p.: 235°–238° C.

EXAMPLE 2

2-Cyanoimino-3-(3-pyridylmethyl)-4-methyl-1,2,3,4-tetrahydro-4H-1,3,4-benzotriazepin-5-one (Method B)

A suspension of 2.15 g (0.01 mole) of 2-cyanoimino-4-methyl-1,2,3,4-tetrahydro-4H-1,3,4-benzotriazepin-5-one, 1.5 g (0.01 mole) of 3-chloromethylpyridine hydrochloride, 2.2 g (0.02 mole) of potassium bicarbonate and 0.1 g of potassium iodide in 10 ml of dimethylformamide is kept at 100° C. for 1 hour. Then it is cooled, 30 ml of chloroform are added and the organic salts are filtered off. The filtrate is poured into 200 ml of water, the organic phase is separated, washed twice with 20 ml of water each, and dried over magnesium sulfate. The solvent is evaporated in vacuo and the residue is crystallized upon adding a slight amount of ether. Thus 1.5 g of the desired product are obtained.

Yield: 42%, m.p.: 231°–232° C.

EXAMPLE 3

2-Benzylamino-4-methyl-3,4-dihydro-4H-1,3,4-benzotriazepin-5-one (Method C)

A solution of 3.2 g (0,015 mole) of 2-cyanoimino-4-methyl-1,2,3,4-tetrahydro-4H-1,3,4-benzotriazepin-5-one and 2.3 g (0.22 mole) of benzylamine in 32 ml of propanol is boiled under stirring and reflux cooling for 14 hours. Then the solvent is evaporated in vacuo, the residue is extracted with a mixture of 60 ml of chloroform and 20 ml of water, the organic phase is washed with water, dried and evaporated. The residue is crystallized upon adding a slight amount of ether. Thus 3.7 g of the desired product are obtained.

Yield: 84%, m.p.: 179°–181° C.

EXAMPLE 4

2-[Amino-(1-piperidinyl)-methyleneamino]-4-methyl-3,4-dihydro-4H-1,3,4 -benzotriazepin-5-one (Method C)

To a hot suspension of 2.15 g (0.01 mole) of 2-cyanoimino-4-methyl-1,2,3,4-tetrahydro-4H-1,3,4-benzotriazepin-5-one in 40 ml of benzene a solution of 0.43 g (0.005 mole) of piperidine in 6 ml of benzene is added within 30 minutes, and the reaction mixture is boiled under stirring and reflux cooling for 1 hour. Then the unreacted starting compound is filtered off and reacted again as described above. When the reaction is complete, the filtrates are combined and evaporated in vacuo and the residue is crystallized from ether. The crude product is subjected to chromatography on silica gel using a 10:2 mixture of chloroform and acetone as solvent mixture. Thus 0.87 g of the desired product is obtained.

Yield: 29%, m.p.: 215°–217° C.

EXAMPLE 5

2-Benzylamino-3-(3-pyridylcarbonyl)-4-methyl-3,4-dihydro-4H-1,3,4-benzotriazepin-5-one (Method D)

A solution of 1.12 g (0.004 mole) of 2-benzylamino-4-methyl-3,4-dihydro-4H-1,3,4-benzotriazepin-5-one in a mixture of 10 ml of anhydrous chloroform and 2 ml of pyridine is added to a solution of 0.53 g (0.004 mole) of nicotinic acid chloride in anhydrous chloroform at 10° C. under stirring, and the reaction mixture is allowed to warm up to room temperature. 48 hours later 50 ml of water are added to the mixture, the organic phase is washed with 0.1 N hydrogen chloride solution and water, dried and evaporated. The residue crystallized from ether. Thus 1.36 g of the desired product are obtained.

Yield: 96%, m.p.: 195°–197° C.

EXAMPLE 6

2-Phenylamino-4-methyl-3,4-dihydro-4H-1,3,4-benzotriazepin-5-one (Method E)

A mixture of 1.2 g (0.004 mole) of 1-(2-aminobenzoyl)-4-phenyl-1-methylthiosemicarbazide and 1.24 g (0.006 mole) of 1,3-dicyclohexylcarbodiimide is boiled in 50 ml of benzene under stirring and reflux cooling for 1 hour. The reaction mixture is then cooled to room temperature and allowed to crystallize for 24 hours. Then it is filtered, the solid product is recrystallized from a 1:1 mixture of dioxane and water, the filtrate is evaporated in vacuo and the residue is crystallized upon adding a slight amount of ether. Thus 0.44 g of the desired product is obtained.

Yield: 41%, m.p.: 207°–209° C.

The 1-(2-aminobenzoyl)-4-phenyl-1-methylthiosemicarbazide used as starting substance can be prepared as follows:

1.65 g (0.01 mole) of 2-amino-N-methylbenzoic acid hydrazide are suspended in 60 ml of benzene, 2.03 g (0.015 moles) of phenyl isothiocyanate are added and the reaction mixture is stirred at room temperature for 5 hours. Thus 2.6 g of the desired compound are obtained.

Yield: 87%, m.p.: 151° C.

EXAMPLE 7 TO 25

On proceeding as specified in Examples 1 to 6 further compounds of the general formula (I) enumerated in the following Table III are prepared. In the general formula (I) of these compounds—with the exception of the products of Examples 13, 14, 16 and 21—the dotted line between the N(1) and C(2) atoms represents a valency bond, consequently substituent $R^1$ is missing.

EXAMPLE 26

2-(3-Pyridylmethylamino)-3-[3-(4-phenyl-1-piperazinyl)-1-propyl]-4-methyl-3,4-dihydro-4H-1,3,4-benzotriazepin-5-one chlorohydrate 0.73 g (0.0015 mole) of the base prepared according to Example 20 is dissolved in the mixture of 1 ml of ethanol and 10 ml of ether, and the solution is adjusted to pH 3 with a 20% solution of hydrogen chloride in ethanol under stirring and ice-cooling. Then further 10 ml of ether are added to the mixture and it is allowed to crystallize overnight. The separated crystals are filtered, washed and dried. Thus 0.88 g of the hygroscopic salt of the base comprising 2.5 moles of water and 2.5 moles of hydrochlocid acid is obtained. Yield: 94%, m.p.: 81°–83 ° C.

TABLE III

| Example No. | R$^1$ | R$^2$ | R$^3$ | R$^4$ | M.p. (°C.) | Yield (%) | Method |
|---|---|---|---|---|---|---|---|
| 7 | — | 2-pyridyl-CH$_2$—NH— | H | CH$_3$ | 194–196 | 70 | C |
| 8 | — | 3-pyridyl-CH$_2$—NH— | H | CH$_3$ | 158–160 | 71 | C |
| 9 | — | (CH$_3$)$_2$—CH—CH$_2$NH— | H | CH$_3$ | 178–180 | 88 | C |
| 10 | — | piperidin-1-yl | H | CH$_3$ | 235–237 | 26 | C |
| 11 | — | Ph—N(piperazine)N—C(NH$_2$)=N— | H | CH$_3$ | 157–158 | 14 | C |
| 12 | — | Ph—N(piperazine)N— | H | CH$_3$ | 213–215 | 21 | C |
| 13 | H | NC—N= | TMPCO(CH$_2$)$_3$— | CH$_3$ | 186–187 | 31 | B |
| 14 | H | NC—N= | 2-pyridyl-CH$_2$— | CH$_3$ | 209–211 | 47 | B |
| 15 | — | 3-pyridyl-CH$_2$—N(CH$_3$)—C(NH$_2$)=N— | H | CH$_3$ | 232–235 | 27 | C |
| 16 | H | NC—N= | Ph—N(piperazine)N—(CH$_2$)$_3$ | CH$_3$ | 126–128 | 50 | B |
| 17 | — | (CH$_3$)$_3$C—CH(CH$_3$)NH—C(NH$_2$)=N— | H | CH$_3$ | 235–236 | 20 | C |
| 18. | — | (CH$_3$)$_3$C—CH(CH$_3$)—NH— | H | CH$_3$ | 247–250 | 33 | C |
| 19 | — | HN-piperidinyl-N=C(NH$_2$)—N= | TMPCO(CH$_2$)$_3$ | CH$_3$ | R$_F$ 0.31$^a$ | 26 | C |
| 20 | — | 3-pyridyl-CH$_2$—NH— | Ph—N(piperazine)N—(CH$_2$)$_3$ | CH$_3$ | R$_F$ 0.43$^b$ | 36 | C |
| 21 | CH$_3$CH$_2$(CH$_3$)CH— | NC—N= | 2-pyridyl-CH$_2$— | CH$_3$ | 101–103 | 39 | B |

TABLE III-continued

| Example No. | R¹ | R² | R³ | R⁴ | M.p. (°C.) | Yield (%) | Method |
|---|---|---|---|---|---|---|---|
| 22 | — | 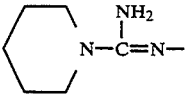 | 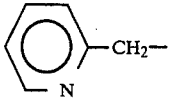 | CH₃ | 188–190 | 52 | C |
| 23 | — | 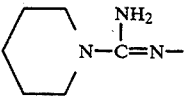 | 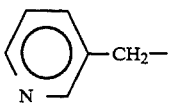 | CH₃ | 221–223 | 60 | C |
| 24 | — | 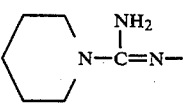 | TMPCO(CH₂)₃— (with C=O) | CH₃ | 209–210 | 19 | C |
| 25 | — | (CH₃)₃C—CH(CH₃)—NH— | 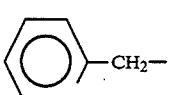 | CH₃ | 194–195 | 38 | C |

The upper indices of the $R_F$ values represent the following mixtures:
<sup>a</sup>: chloroform-methanol-triethylamine = 6:1:1
<sup>b</sup>: ethyl acetate-methanol = 1:1
TMP stands for 3,4,5-trimethoxyphenyl

What we claim is:

1. A racemic 1,3,4-benzotriazepin-5(4H)-one selected from the group consisting of
   (a) 2-(amino-(1-piperidinyl)-methyleneamino)-4-methyl-3,4-dihydro-1,3,4-benzotriazepin-5(4H)-one,
   (b) 2-(amino-(3,3-dimethyl-2-butylamino)-methyleneamino)-4-methyl-3,4-dihydro-1,3,4-benzotriazepin-5(4H)-one,
   (c) 2-(amino-(1-homopiperazinyl)-methyleneamino)-3-(3-(3,4,5-trimethoxybenzoyloxy)-1-propyl)-4-methyl-3,4-dihydro-1,3,4-benzotriazepin-5(4H)-one,
   (d) 2-(3,3-dimethyl-2-butylamino)-4-methyl-3,4-dihydro-1,3,4-benzotriazepin-5(4H)-one,
   (e) 2-(amino-(1-piperidinyl)-methyleneamino)-3-(2-pyridyl-methyl)-4-methyl-3,4-dihydro-1,3,4-benzotriazepin-5(4H)-one
   (f) 2-(3-pyridylmethylamino)-3-(3-(4-phenyl-1-piperazinyl)-1-propyl)-4-methyl-3,4-dihydro-1,3,4-benzotriazepin-5(4H)-one,
   and acid addition salts thereof.

2. A method of treating angina pectoris, which comprises administering to a patient an effective amount of a compound of claim 1 or a pharmaceutically acceptable salt thereof, said amount being effective to treat angina pectoris.

3. The method according to claim 2, wherein said effective amount is 0.2–25 mg/kg bodyweight daily.

4. The method according to claim 3, wherein said effective amount is 0.2–10 mg/kg bodyweight daily.

5. A pharmaceutical composition comprising as active ingredient a therapeutically effective amount to treat angina pectoris of a racemic compound of claim 1, or an acid-addition salt thereof together with one or more pharmaceutically acceptable carrier(s), diluents(s) and/or excipient(s).

* * * * *